United States Patent [19]
Ishiwata et al.

[11] Patent Number: 5,730,971
[45] Date of Patent: Mar. 24, 1998

[54] POTENTIATOR FOR INTERFERON AND AN ANTIVIRAL ACTIVITY-POTENTIATING COMPOSITION CONTAINING INTERFERON AND ITS POTENTIATOR

[75] Inventors: Yoshiro Ishiwata; Takahito Jomori, both of Aichi-ken; Hidetsugu Saito, Tokyo; Takahiko Mitani; Kiichi Sawai, both of Aichi-ken, all of Japan

[73] Assignee: Sanwa Kagaku Kenkyusho Co., Ltd., Aichi-ken, Japan

[21] Appl. No.: 361,442

[22] Filed: Dec. 20, 1994

[30] Foreign Application Priority Data

Dec. 27, 1993 [JP] Japan ................... 5-332630

[51] Int. Cl.$^6$ .................................. A61K 38/21
[52] U.S. Cl. .............. 424/85.4; 424/85.5; 424/85.6; 424/85.7
[58] Field of Search ................. 424/85.4, 85.5, 424/85.6, 85.7

[56] References Cited

U.S. PATENT DOCUMENTS 5,550,111  8/1996  Suhadolnik et al. ............ 514/44

FOREIGN PATENT DOCUMENTS 2676648  11/1992  France .
127811   11/1978  Japan .
4-200400  7/1992  Japan .
WO 92/17173  10/1992  WIPO .

OTHER PUBLICATIONS

"The 5'-Terminal Sequence of the Hepatitis C Virus Genome," Japan J. Exp. Med. vol. 60, 3, pp. 167–177, 1990, Hiroaki Okamoto et al.

"Potentiation of the Antiviral Activity of Poly r(A–U) by Riboflavin, FAD and FMN," Cell Biology International Reports, vol. 13, No. 2, pp. 215–222, Feb. 1989, James M. Jamison et al.

"Phage–inactivating Effect of Riboflavin Phosphate and Flavin–adenine Dinucleotide," Agri. Biol. Chem., 49 (6), pp. 1881–1883, 1985, Akira Murata et al.

Niisawa et al., Clin. Report, vol. 19(8), pp. 4287–4293, 1985.

Hoofnagle et al., J. Hepatol., vol. 17/Suppl. 3, pp. S130–S136, 1993.

Davis et al., The New England J. Med., vol. 321(22), pp. 1501–1506, 1989.

Bisceglie et al., The New England J. Med., vol. 321(22), pp. 1506–1510, 1989.

*Primary Examiner*—Chhaya D. Sayala
*Attorney, Agent, or Firm*—Nikaido Marmelstein Murray & Oram LLP

[57] ABSTRACT

A potentiator for interferon and an antiviral activity-potentiating composition containing interferon and its potentiator are provided. The potentiator is a mixture of flavin adenine dinucleotide (FAD) and porcine liver extract.

6 Claims, No Drawings

5,730,971

1

POTENTIATOR FOR INTERFERON AND AN ANTIVIRAL ACTIVITY-POTENTIATING COMPOSITION CONTAINING INTERFERON AND ITS POTENTIATOR

BACKGROUND OF THE INVENTION (1) Field of the Invention

The present invention relates to a potentiator for interferon and an antiviral activity-potentiating composition comprising interferon and its potentiator.

(2) Related Arts

The term "interferon" (hereinafter also refers to as "IFN") has been adopted to refer to the generic name for glycoproteins which are produced and secreted by animal cells infected with virus, and the like.

Interferons are classified into three types. Type α is induced in leukocyte by virus infection or nucleic acid treatment. Type β is induced by a similar fibroblast and has a structure similar to that in type α. Type γ is induced in lymphocyte by stimulation with specific antigens or mitogen and thus said as "immune interferon". Interferons can be extracted from natural materials, or produced by a genetic recombination technique with the aid of animal cells or $E.\ coli$, and has been marketed under Trademarks of "Feron", "Sumiferon", "Canferon", "Roleton", "Intron", and the like.

Although human interferons are used as a tumor-treating drug, they are also utilized as a drug for treating chronic vital hepatitis B and C; however, the efficacy of interferons for treating chronic hepatitis B is unsatisfactory, and the rate of efficacy is at most 30% in the case of chronic hepatitis C. In addition, human interferons are too expensive, and restrictions on their use are under discussion from the viewpoint of reduction in medical expenses for treating such chronic hepatitis.

On the other hand, the assignee company of the present invention has marketed a composition as a hepatitis-treating drug under the trademark "Adelavin No. 9" which comprises 15 μl/ml of porcine liver extract and 10 mg/ml of flavin adenine dinucleotide (FAD). The "Adelavin No. 9" has been marketed for the purpose of protecting the liver, but the potentiating effect on the antiviral activity of interferon has been unknown.

A report has been issued on the potentiating activity of FAD, which is one of components of "Adelavin No. 9", on the anti-vesicular stomatitis virus (VSV) activity of POLYr (A–U) which is one of interferon inducers ["Cell Biol. Int. Rep.", Vol. 13, pages 215–222 (1989)]. In addition, as reported in "Agric. Biol. Chem.", Vol. 149, No. 6, pages 1881–1883 (1985), riboflavin (vitamin $B_2$) which constitutes a part of the structure for FAD and liver extract have been shown to exhibit an antiviral action [WO 92/17173(A) and FP 2,676,648]; however, the effect of them on the antiviral action of interferon has not been investigated.

In addition to the high drug price of interferon, such an economic problem has arisen that it shows low effectiveness in treating intractable chronic hepatitis B and C, as described above.

SUMMARY OF THE INVENTION

Thus, it is a principal object of the invention to provide a potentiator for interferon, which can draw out the desirable pharmacological activity of interferon in smaller amount.

Another related and important object of the invention is to provide an antiviral activity-potentiating composition comprising interferon and its potentiator.

2

The aforesaid "Adelavin No. 9" (Trademark) has been administered to protect liver injury: however, when patients with chronic vital hepatitis C receive the "Adelavin No. 9", the images of hepatic tissue have been shown to improve.

In this respect, the inventors have intensively investigated on the relationship between "Adelavin No. 9" and virus infection, and as a result, have unexpectedly found that "Adelavin No. 9" significantly potentiates the antiviral activity of interferon. The present invention has been completed on the basis of this finding.

Further, the inventors have investigated in detail on "Adelavin No. 9", and have found that the enhancing activity of interferon action is not caused by polypeptides in the liver extract, but mainly by the FAD component of "Adelavin No. 9", and that "Adelavin No. 9" and FAD tested individually potentates the antiviral activity of interferon without being administered combinationally with interferon. This suggests strongly that flavin adenine mononucleotide (FMN) and riboflavin which constitute parts of the structure for FAD may also contribute to potentiate the activity of interferon.

DETAILED DESCRIPTION OF THE INVENTION

According to the invention, the foregoing principal object may be attained by providing a potentiator for interferon, wherein the potentiator is selected from the group consisting of a mixture of porcine liver extract and flavin adenine dinucleotide (FAD); FAD per se; flavin adenine mononucleotide (FMN); riboflavin (vitamin $B_2$); and a mixture thereof.

The foregoing related and important object of the invention can be attained by providing a composition comprising interferon and its potentiator.

The potentiator for interferon of the invention may be administered separately or independently in advance of the administration of interferon, or administered simultaneously with interferon in the form of compositions thereof. When being administered separately, the potentiator is first consecutively given 3 to 5 days, thereafter interferon is administered the day after the last administration of potentiator.

Any commercially available interferon may be used, and when an interferon/potentiator combination is used as a composition, e.g., when a combination of interferon ["Canferon" (Trademark)] and "Adelavin No. 9" is used, the amount of "Canferon" to be mixed with 2 ml of "Adelavin No. 9" as the potentiator is 3,000,000, 6,000,000, or 9,000,000 IU. Any type of interferon, e.g., type α, β, or γ may be used.

Albumin and the like may be incorporated into an injection. Further, the preparations may be in the form of solid preparations including oral drugs such as tablets and capsules. In this case, the Solid preparations contain liver extract, FAD, FMN, and riboflavin individually or combinationally.

DETAILED DESCRIPTION OF PREFERRED EMBODIMENTS

The invention will now be explained in more detail by following Examples and Test Examples.

EXAMPLE 1

(Potentiator for Interferon Activity "Injection")

Two ml of a solution containing 15 μl/ml of porcine liver extract and 10 mg/ml of FAD (pH 6.0±0.5, osmotic pressure ratio: about 1) were aseptically charged into ampules which were thermally sealed to prepare ampuled injections.

The prescription of this preparation is same with that for the commercial product of "Adelavin No. 9". When being used, the preparation shall be dissolved in a 5%-glucose solution or conventional supplemental solution to dose the same through a drip infusion.

EXAMPLE 2

(Potentiated Interferon Preparation "Injection")

A preparations was prepared in accordance with the following prescription by aseptically charging the ingredients into each ampule. When being used, the preparation shall be dissolved in a 5%-glucose solution or conventional supplemental solution to dose the same through a drip infusion.

| Ingredients | |
|---|---|
| "Adelavin No. 9" (Trademark) | 2 ml |
| "Canferon" (Trademark) | $3 \times 10^6$ IU |
| Human serum albumin | 5 mg |

Test Example 1

[Effect on anti-herpes simplex virus type 1 (anti-HSV-1)]

The effect of "Adelavin No. 9" on anti-HSV-1 activity of interferon was investigated in vitro culture system.

(1) Procedure

"Adelavin No. 9" (Trademark) and human interferon-α-2a ["Canferon" (Trademark)] were added to mondayer of HeLa cells cultured in a microplate with 96 wells, thereafter the cells were cultured at 37° C. in an atmosphere containing 5% $CO_2$ in air for 20 hours and then infected with HSV-1 MIYAMA strain in a dose of 100 $LD_{50}$, and "Adelavin No. 9" and "Canferon" were further added, and the cells were cultured for two days. After fixation and staining, cytopathic effect (CPE) by HSV-1 was examined microscopically, and the anti-HSV-1 activity ($IC_{50}$) of interferon-α-2a was measured.

(2) Results and Discussion

The results given in Table 1 show that "Adelavin No. 9" potentiates the anti-HSV-1 activity of interferon-α-2a in concentration dependent fashon, i.e., the activity is potentiated 2-, 8- and 64-folds by 1.25, 2.5 and 5.0 μl/ml, respectively.

TABLE 1

| | Conc. of "Adelavin No. 9" (μl/ml) | | | |
|---|---|---|---|---|
| | 0 | 1.25 | 2.5 | 5.0 |
| Anti-HSV-1 activity of IFN ($IC_{50}$, IU/ml) | 100 | 50 (2-folds) | 1.25 (8-folds) | 1.6 (64-folds) |

Test Example 2

Further, "Adelavin No. 9" contains FAD in an amount of 10 mg/ml, as referred to before; therefore, a 10 mg/ml FAD solution was prepared separately, and the procedure described in Test Example 1 was followed. The results given in following Table 2 show that FAD alone activates the anti-HCV-1 activity of interferon-α-2a, dependently in its concentration.

TABLE 2

| | Concentration of FAD (μl/ml) | | | |
|---|---|---|---|---|
| | 0 | 1.25 | 2.5 | 5.0 |
| Anti-HSV-1 activity of IFN ($IC_{50}$, IU/ml) | 100 | 50 (2-folds) | 18.8 (5-folds) | 4.7 (21-folds) |

Test Example 3

(Inhibitory Effect on Replication of HSV-1)

The effects of "Adelavin No. 9" (Trademark) and FAD on the inhibitory effect of interferon against HSV-1 replication were investigated using in vitro culture system.

(1) Procedure

"Adelavin No. 9" or 10 mg/ml of FAD solution, and human interferon-α-2a ["Canferon" (Trademark)] were added to mondayer of HeLa cells cultured in a microplate with 24 wells, thereafter the cells were incubated at 37° C. in an atmosphere containing 5% $CO_2$ in air for 24 hours. After removal of the drugs, the cells were infected with HSV-1 MIYAMA strain and cultured for 2 days, and then, an amount of the virus in supernatant of the culture medium was measured by the plaque assay.

(2) Results and Discussion

Results show that "Adelavin No. 9" increases the inhibitory effect of interferon-α-2a (44%) on the replication of HSV-1 [interferon-α-2a (6.25 IU/ml)], dependently in its concentra- tion, i.e., an 83 and 96% increase in 1.25 and 5.0 μl/ml, respectively, and a FAD solution also increases the inhibitory effect of interferon-α-2a (44%), i.e., a 70 and 86% increase in 1.25 and 5.0 μl/ml, respectively.

Test Example 4

(Anti-Influenza Virus Activity)

The effects of "Adelavin No. 9" (Trademark) and FAD on the inhibitory effect of interferon-α-2a against INFV replication were investigated by using influenza virus (INFV) A/PR/8 strain.

(1) Procedure "Adelavin No. 9" or 10 mg/ml FAD solution, and human interferon-β-2a ["Canferon" (Trademark)] were added to monolayer of MRC-5 cells cultured in a microplate with 24 wells, thereafter the cells were further incubated at 37° C. in an atmosphere containing 5% $CO_2$ in air for 20 hours. After removal of the drugs, the cells were infected with INFV and cultured for 3 days. Then, an amount of the virus in supernatant of the culture medium was measured by the hemagglutination assay (HA).

(2) Results and Discussion

Results show that "Adelavin No. 9" increases the inhibitory effect of interferon-α-2a on the replication of INFV dependently in its concentration; i.e., an interferon/ "Adelavin No. 9" (0.63 μl/ml) combination exhibits a 50 and 83% inhibition rate of INFV proliferation, respectively, and an interferon/FAD solution (0.73 μl/ml) combination exhibits a 33.4 and 79.1% inhibition rate of INFV proliferation, respectively, whereas interferon-α-2a (1.56 and 6.25 IU/ml) exhibits a 17 and 58% HAU (hemagglutination unit) inhibition rate.

Test Example 5

[Anti-Hepatitis B Virus (Anti-HBV) Activity]

The combination effect of interferon-α-2a ["Canferon" (Trademark)] and "Adelavin No. 9" (Trademark) on HBV was investigated by using HBV genome-integrated HB-611 cells.

(1) Procedure

An amount of HBV genome in HB-611 cells cultured with interferon-α-2a and "Adelavin No. 9" was measured.

That is, HB-611 cells were cultured on a microplate with 6 wells in a rate of $1.5 \times 10^5$ cells/well. The addition of IFN-α-2a and "Adelavin No. 9" was started on the fourth day when a monolayer had been observed to form. The cultivation was allowed to continue for 18 days, while the culture medium containing the drugs was exchanged every 3 days.

Thereafter, the cells were treated with proteinase K and ribonuclease, and the DNA was extracted with phenol. The extracted DNA was treated with restriction enzyme of HindIII and then transferred to hybridize with HBV-DNA probe labeled with $^{32}$P-dCTP. A FUJI BSA2000 (Trademark) bioimaging analyzer was employed for detecting DNA bands thereby calculating HBV production ratio from a radio activity of free HBV and radio activity of genome HBV to determine rate of HBV production inhibition by the drugs.

(2) Results and Discussion

The results, given in Table 3, show that "Adelavin No. 9" can potentiate the inhibitory effect of interferon-α-2a on the HBV transcription, dependently to its concentration.

TABLE 3

| | | Conc. of IFN-α-2a (IU/ml) | | | |
|---|---|---|---|---|---|
| | | 0 | 50 | 200 | 400 |
| "Adelavin No. 9" | 0 | 0 | 4 | 19 | 25 |
| concentration | 2.0 | 0 | 12 | 27 | 28 |
| (µl/ml) | 10.0 | 0 | 17 | 36 | 44 |

The results obtained by Test Examples 1–5 suggest strongly that both "Adelavin No. 9" and FAD potentiate the activity of interferon to both DNA and RNA viruses in vitro, and riboflavin which forms a part of the structure for FAD also potentiates the activity of interferon.

This observation led to following in vivo experiments.

Test Example 6

(Combination Effect of INF-α and "Adelavin No.9" on mouse infected with HSV-1)

(1) Procedure

C3H/HeN mice were used in this experiment. They were grouped so that one group consists of 10 mice. Mouse INF-α and "Adelavin No.9" (Trademark) were mixed together, and the resulting mixture was injected intraperitoneally. After 20 hours, the mice were infected with HSV-1 MIYAMA strain in a dose of 10 $LD_{50}$.

The moralities were observed for 20 days and the rate of survival at that stage was calculated.

(2) Results and Discussion

The results given in following Table 4 show that administration with combination of INF-α/"Adelavin No. 9" (60 µl) significantly prolongs the average of survival days, whereas the the treatment with INF-α ($2.5 \times 10^3$ IU) alone had no significant action.

TABLE 4

| Dosage/mouse | Average of survival days |
|---|---|
| Control | 10.6 ± 1.7 |
| INF-α ($2.5 \times 10^3$ IU) | 14.0 ± 1.8 |
| INF-α ($2.5 \times 10^3$ IU) + "Adelavin No. 9 (60 µl) | 16.4 ± 1.6(*) |

In the Table, (*): there is a significant difference to control by the Mann-Whitey's U-test (p < 0.05).

Test Example 7

(Clinical Test)

(1) Summary

An amount of HCV (human hepatitis C virus) in serum obtained from patients with chronic hepatitis C through clinical test, who have been administered with an interferon and "Adelavin No. 9" (Trademark) in combination was measured by utilizing so called "the polymerase chain reaction (PCR) technique". In order to estimate the antiviral effect of the above combination semiquantitatively, a series of dilutions of the serum decreasing by each 1/10 in concentration was prepared, and the amount of HCV was given as PCR titer as expressed by the maximum dilution ratio detectable by PCR.

In both groups, wherein patients received interferon [INF "Sumiferon" (Trademark)] alone and patients received in a combination of "Adelavin No. 9" (Trademark) and INF "Sumiferon", it was recognized that the average of PCR titers becomes to decrease; however, in the combinationally administered group, the average decreased one to two orders of magnitude in 9 cases of all the 10 cases, indicating that there was a significant difference in 5% one-sided t-test between the two groups.

(2) Purpose

The following trial were designed to assess the antiviral effect of an interferon/"Adelavin No.9" (ADE9) combination on patients suffering from chronic hepatitis C by measuring the amount of HCV in the serum of the patients.

(3) Procedure (A) Group classification

Group I: INF (once Intramuscular injection, 6 MIU), 10 individuals.

Group II: ADE9 [daily intravenous injection for 5 days, one ampule (2 ml)/once/day +IFN (once intramuscular injection, 6 MIU), 10 individuals.

(B) Schedule for collecting blood and administration of drugs

Table 5 shows the schedule for collecting blood and administration of days in both groups.

TABLE 5

| | | Day | | | | | | | | |
|---|---|---|---|---|---|---|---|---|---|---|
| Gr. | Item | −1 | 0 | 1 | 2 | 3 | 4 | 5 | 6 | 7 |
| I | Administration of IFN | | | | | | | ↓ | | |
| | Collection of blood | | | | | | | | ↓ | ↓ |
| II | Administration of | | | | | | | | | |
| | ADE9 | | ↓ | ↓ | ↓ | ↓ | ↓ | | | |
| | IFN | | | | | | | ↓ | | |
| | Collection of blood | ↓ | | | | | | | ↓ | ↓ |

In Table 5, the administration of IFN on 5th day was conducted after the collection of blood on that day.

(C) Specimen or Sample

Such a 10-folds dilution system ($10^1$–$10^5$ folds) of the serum of the patient with HCV was prepared by using serum obtained from healthy individuals and the resulting diluted serums were used as specimens.

(D) PCR method

The procedure used in this test was an improved one which developed by the inventors [Jap. Pat. No. Hei 4 (A.D. 1992)-200400(A)]. The entire reaction from RNA extraction to PCR occurs in only one reaction tube; i.e., a specimen and reagents of five kinds (Reagents A, B, C, D and E) are added stepwise to the reaction tube, and the solution are allowed to react without being taken out from the reaction tube.

Further, all reactions were carried out in a "Thermal cycler" (Trademark, Perkin-Elmer Cetus Corporation).

(a) Preparation of reagents

The following reagents were prepared.

(i) Reagent A (Solution for dissolving specimen):

A solution consisting of 125 mM Tris-hydroxyaminomethane HCl buffer (pH 8.0), 62.5 mM KCl, 7.5 mM $MgCl_2$, 2.5 mg/ml proteinase K, and 0.02% "Triton X-100" (Trademark).

(ii) Reagent B (Primer solution for first PCR)

A 50 mM Tris-hydroxyaminomethane HCl buffer solution (pH 8.0) containing 1 µM sense primer of the sequence 5'-ACTCCACCATAGATCACTCC-3' (SEQ ID No. 1) corresponding to the 7–26th region of the 5'-noncoding region in the nucleotide sequence of HCV genome [as reported by Okamoto, et al. in "Jpn. J. Exp. Med." Vol. 60, pages 167–177 (1990)], and 1 µM antisense primer of the sequence 5'-AACACTACTCGGCTAGCAGT-3' (SEQ ID No. 2) corresponding to the 229–248th region of from the 5'-noncoding region to the core region in the nucleotide sequence.

(iii) Reagent C (Reverse transcriptase solution)

A solution containing 50 mM Tris-hydroxyaminomethane HCl buffer (pH 8.0), 50 mM KCl, 15.75 mM dithiothreitol, 3.94 mM deoxyadenosine 5'-triphosphate, 3.94 mM deoxyguanosine 5'-triphosphate, 3.94 mM deoxycytidine 5'-triphosphate, 3.94 mM deoxythymidine 5'-triphosphate, 26.5 mM $MgCl_2$, 10 units AMV-derived reverse transcriptase, and 20 units RNase inhibitor.

(iv) Reagent D (Reactant solution for PCR)

A solution containing 10 mM Tris-hydroxyaminomethane HCl buffer (pH: 8.9), 242.1 mM KCl 4.53 mM $MgCl_2$, 1.143mg/ml bovine serum albumin, 0.2294 cholic acid, 0.2294 "Triton X-100"(Trademark), and 4.8 units Tth DNA polymerase.

(v) Reagent E (Primer solution for second PCR)

A solution containing 150 nM sense primer of the sequence 5'-TCTTCACGCAGAAAGCGTCTAGCCA-3' (SEQ ID No. 3) corresponding to the 44–69th region of the 5'-noncoding region in the nucleotide sequence of HCV genome as described above, 150 nM anti-sense primer of the sequence 5'-CAATTCCGGTGTACTCACCGGTTCC-3' (SEQ ID No. 4) corresponding to the 135–159th region of from the 5'-noncoding region to the core region in the nucleotide sequence, 10 mM Tris-hydroxyaminomethane HCl buffer (pH 8.9), 40 mM $CaCl_2$, 2.8 mM $MgCl_2$, 300 nM deoxyadenosine 5'-triphosphate, 300 nM deoxyguanosine 5'-triphosphate, 300 nM deoxycytidine 5'-triphosphate, 300 nM deoxythymidine 5'-triphosphate, 0.5 mg/ml bovine serum albumin, 0.1% cholic acid, 0.1% "Triton X-100" (Trademark), and 4.8 units Tth DNA polymerase.

(b) Experimental procedure

Into a 0.6m sterilized reaction tube was charged each specimen (30 µl ), followed by addition of the reagent A (20 µl ) and a mineral oil (100 µl ). The contents were vigorously stirred by a vortex mixer for 5 seconds. After being centrifuged lightly at 4000 rpm/min for one second (thereafter centrifugation was carried out under the same conditions), the contents were allowed to react at 55° C. for 60 minutes thereby giving a virus genome extract.

Into the reaction tube containing the virus genome extract was added 20 µl of the reagent B, followed by centrifugation after stirring. The proteinase K was deactivated by keeping the contents at 99° C. for 15 minutes, after which the contents were cooled to 20° C. thereby annealing the primer to the virus genome.

Into the reaction tube was further added 20 µl of the reagent C. The contents were stirred lightly and centrifuged, and then allowed to react at 45° C. for 60 minutes thereby providing the DNA (cDNA) complementary to the virus genome.

To the solution containing the cDNA and the primer was added 70 µl of the reagent D, thereafter the contents were mixed by overturning 5 times. After being centrifuged, the contents were allowed to perform the first PCR of 40 cycles. Although the KCl concentration in the reagent D was 242.1 mM as described above, the final concentration was 120 mM because of dilution during the steps described above.

The PCR conditions were at 94° C. for 3 minutes, at 55° C. for 1.5 minutes, and at 72° C. for one minute for the first one cycle, and at 94° C. for one minute, at 55° C. for 1.5 minutes, at 72° C. for one minute for the following 39 cycles. The temperature of the contents were kept at 20° C. after the PCR.

To the amplified DNA-containing reactant solution was added 160 µl of the reagent E. The contents were mixed by overturning 5 times followed by centrifugation. The second PCR of 40 cycles was performed at 94° C. for one minute at 55° C. for 1.5 minutes, and at 72° C. for one minute. The temperature was kept at 20° C. after the PCR.

Detection of the amplified PCR products was carried out by a 0.1% sodium dodecyl sulfate-8% polyacryloamide gel electrophoresis. The mixture of the reactant solution (10 µl) and a 30% glycerol solution (2 µl) containing 0.25% bromophenol blue was applied to the gel to perform electrophoresis at 200 W constant-voltage for 25 minutes. The gel was immersed in tap water for 10 minutes in order to remove the sodium dodecyl sulfate from the gel, followed by immersion in a 0.5 µg/ml ethidium bromide solution for 10 minutes to stain the DNA. The detection of the products was carried out by the fluorescence microscopy by visualizing under 312 nm ultraviolet light. When a band was found at 116 bp, the specimen was judged as positive.

(C) The amount of HCV

The amount of HCV was given as PCR titer as expressed by the maximum dilution ratio detectable by PCR.

(4) Results

Results are shown in following Table 6. It has been found that there is a 5% significant difference in the one-sided t-test between the two groups wherein one group received interferon alone and another group received a combination of interferon and "Adelavin No. 9".

TABLE 6

| Gr. | Patient | PCR titer Administration | | | Change ratio of titer | Mean titer ratio among groups |
|---|---|---|---|---|---|---|
| | | ADE9 before | IFN before | IFN after | | |
| I | a | | $10^3$ | $10^1$ | $10^2$ | $10^{1.1\pm0.2}$ |
| | b | | $10^4$ | $10^3$ | $10^1$ | |
| | c | | $10^1$ | $10^0$ | $10^1$ | |
| | d | | $10^4$ | $10^2$ | $10^2$ | |
| | e | | $10^4$ | $10^2$ | $10^2$ | |
| | f | | $10^2$ | $10^1$ | $10^1$ | |
| | g | | $10^3$ | $10^3$ | $10^0$ | |
| | h | | $10^3$ | $10^2$ | $10^1$ | |
| | i | | $10^4$ | $10^3$ | $10^1$ | |
| | j | | $10^2$ | $10^2$ | $10^0$ | |
| II | k | $10^2$ | $10^1$ | $10^2$ | $10^0$ | $10^{1.8\pm0.3(*)}$ |
| | l | $10^2$ | $10^2$ | $10^0$ | $10^2$ | |
| | m | $10^4$ | $10^2$ | $10^1$ | $10^3$ | |
| | n | $10^3$ | $10^2$ | $10^1$ | $10^2$ | |
| | o | $10^3$ | $10^2$ | $10^2$ | $10^1$ | |
| | p | $10^2$ | $10^2$ | $10^1$ | $10^1$ | |
| | q | $10^3$ | $10^2$ | $10^1$ | $10^2$ | |
| | r | $10^3$ | $10^3$ | $10^0$ | $10^3$ | |
| | s | $10^4$ | $10^3$ | $10^1$ | $10^3$ | |
| | t | $10^1$ | $10^1$ | $10^0$ | $10^1$ | |

In the Table, *: there is a significant difference from Group I in the one-sided t-test ($p < 0.05$).

What is claimed is:

1. A method for improving the antiviral activity of interferon, comprising administering interferon and a potentiator composition comprising porcine liver extract and flavin adenine dinucleotide.

2. The method according to claim 1, wherein said interferon is selected from the group consisting of human interferon types $\alpha$, $\beta$, and $\gamma$.

3. The method according to claim 1, wherein said interferon and said potentiator composition are administered separately.

4. A method for treating a viral infection, comprising administering to a patient in need of such treatment, an effective amount of interferon and a composition which comprises porcine liver extract and flavin adenine dinucleotide.

5. The method according to claim 4, wherein said interferon and said potentiator composition are administered separately.

6. The method according to claim 4, wherein said viral infection is chronic viral hepatitis B or C.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 20 nucleic acids
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:1:

ACTCCACCAT AGATCACTCC    20

( 2 ) INFORMATION FOR SEQ ID NO:2:

( i ) SEQUENCE CHARACTERISTICS:
        ( A ) LENGTH: 20 nucleic acids
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:2:

AACACTACTC GGCTAGCAGT    20

( 2 ) INFORMATION FOR SEQ ID NO:3:

( i ) SEQUENCE CHARACTERISTICS:
        ( A ) LENGTH: 25 nucleic acids
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:3:

TCTTCACGCA GAAAGCGTCT AGCCA 25

( 2 ) INFORMATION FOR SEQ ID NO:4:

( i ) SEQUENCE CHARACTERISTICS:
        ( A ) LENGTH: 25 nucleic acids
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:4:

CAATTCCGGT GTACTCACCG GTTCC 25